United States Patent [19]

Asano

[11] Patent Number: 5,555,198
[45] Date of Patent: Sep. 10, 1996

[54] APPARATUS FOR COUNTING PARTICLES

[75] Inventor: Kaoru Asano, Nishi-ku, Japan

[73] Assignee: Toa Medical Electronics Co., Ltd., Kobe, Japan

[21] Appl. No.: 466,371

[22] Filed: Jun. 6, 1995

Related U.S. Application Data

[62] Division of Ser. No. 900,449, Jun. 18, 1992.

[30] Foreign Application Priority Data

Nov. 27, 1991 [JP] Japan ................................. 3-339707

[51] Int. Cl.$^6$ ................................................. G01N 27/27
[52] U.S. Cl. ................ 364/555; 364/413.1; 364/413.07; 364/413.08; 382/133; 382/128
[58] Field of Search ................................. 364/555, 413.1, 364/413.07–.09; 382/128, 133; 324/71.4; 436/10, 17; 377/10–12; 356/39; 395/900, 924

[56] References Cited

U.S. PATENT DOCUMENTS

| | | | |
|---|---|---|---|
| 3,515,884 | 6/1970 | Imadate et al. | 377/12 |
| 4,475,236 | 10/1984 | Hoffman | 382/134 |
| 4,661,913 | 4/1987 | Wu et al. | 364/500 |
| 4,882,284 | 11/1989 | Kirchanski et al. | 436/63 |
| 4,987,086 | 1/1991 | Brosnan et al. | 436/501 |
| 4,991,092 | 2/1991 | Greensite | 364/413.13 |
| 5,121,338 | 6/1992 | Lodder | 364/498 |
| 5,187,673 | 2/1993 | Carver, Jr. et al. | 364/555 |
| 5,308,772 | 5/1994 | Sakata et al. | 436/17 |
| 5,329,461 | 7/1994 | Allen et al. | 324/71.4 |
| 5,432,885 | 7/1995 | Nomoto et al. | 395/900 |

OTHER PUBLICATIONS

R. Giles, "The Concept of Grade of Membership", Fuzzy Sets and Systems 25 (1988), pp. 297–323, North–Holland.

J. Key et al., "Cloud Classification from Satellite Data Using a Fuzzy Sets Algorithm: A Polar Example", International Journal of Remote Sensing, Dec. 1989, UK, vol. 10, Nr. 12, pp. 1823–1842, ISSN 0143–1161.

J. Bezdek et al., "Core Zone Scatterplots: A New Approach to Feature Extraction for Visual Displays", Computer Vision, Graphics, and Image Processing 41, pp. 186–209 (1988).

Y. Lim et al., "On the Color Image Segmentation Algorithm Based on the Thresholding and the Fuzzy c–Means Techniques", Pattern Recognition, vol. 23, No. 9, pp. 935–952, 1990.

Primary Examiner—James P. Trammell
Assistant Examiner—Hal D. Wachsman
Attorney, Agent, or Firm—Banner & Allegretti, Ltd.

[57] ABSTRACT

A method of seeking the number of particles of each kind in a group of particles in which plural kinds of particles are intermixed, by measuring, for example, two kinds of properties of each particle by a suitable method or device, plotting each particle on a rectangular co-ordinate system using the measured properties as its X and Y co-ordinates to obtain a distribution diagram, drafting boundaries to partition the distribution into clusters of the respective kinds and counting the number of particles within the boundary of each cluster, which, especially, even when the clusters of the respective particles are mutually overlapping, can reduce any deviation of the count of particles from its true value as small as possible by defining an optimum boundary. In this method, a center of gravity of each cluster is determined, a degree of attribution of each particle to each cluster is calculated based upon a distance of each particle from the center of gravity and the number of particles belonging to each cluster is counted in consideration of the degree of attribution.

4 Claims, 3 Drawing Sheets

APPARATUS FOR COUNTING PARTICLES

This application is a divisional of Ser. No. 07/900,449, filed Jun. 18, 1992.

BACKGROUND OF INVENTION

This invention relates to a method and Apparatus for of separately counting the respective numbers of particles of plural kinds included in the same specimen and, for example, to a so-called blood cell counting method for seeking the numbers of lymphocytes, monocytes and granulocytes in white blood cells.

Such prior art blood cell counting has been effected as follows, as disclosed, for example, in the U.S. Pat. No. 4,661,913. Blood extracted from a human body is first subjected to a predetermined preliminary-treatment to provide a specimen and it is supplied to a suitable particle detector to measure two kinds of properties of each blood cell. Then, a suitable XY co-ordinate system is established and the blood cell is plotted on the co-ordinate system using two kinds of measured values-thereof as its X and Y co-ordinates, respectively. All blood cells in the specimen are plotted in the same manner to produce a distribution diagram, so-called "scattergram", of the particles regarding both properties as above-mentioned. Thereafter, boundaries for partitioning clusters of the respective blood cells, namely, lymphocytes, monocytes and granulocytes are drafted on the scattergram and the number of plots within each boundary is then counted.

In this method, it is easy to define the boundaries and highly accurate count values are obtainable when the clusters of the respective kinds of blood cells are clearly separated from each other on the scattergram. When the respective clusters are mutually close or overlapping as in conventional scattergrams, however, it is difficult to define the boundaries uniquely without use of any auxiliary knowledge and information and the counting accuracy is reduced since the count of each kind of blood cells varies with the mode of selection of the boundary. Moreover, the auxiliary knowledge and information are obtained experientially in accordance with the kind of particles and have no universality in use and a lot of labor and time are needed for prepartion thereof.

In order to remove this problem, a fuzzy clustering method in which any plot unclearly belonging to a specific cluster is assigned partially to two or more clusters has been proposed. Although this method is suitable for analyzing the distribution since fuzziness can be expressed naturally, it has such a problem in that a very long operation time due to complicated algorithm is needed and, for example, even a personal computer having a thirty-two bit central processing unit may need a time as long as one minute or more.

SUMMARY OF INVENTION

Accordingly, an object of this invention is to provide an improved clustering method which can obtain accurate count calues from the above-mentioned scattergram of the particles within a relatively short operation time.

Also, in the method of this invention, any plot unclearly belonging to a specific cluster is assigned to two or more clusters at the same time. An extent to which it is assigned is referred to as "membership (value)" and this membership has a value of one when the plot belongs to a single cluster and a positive value less than one when it belongs to two or more clusters.

A closed fixed domain is defined first at the position of a specific cluster on the scattergram so that, at least, any particle enclosed therein belongs to the cluster and, therefore, its membership to the cluster is one, and a center of gravity of the cluster is calculated from the particles included therein with a predetermined algorithm. Next, distances from the respective particles outside the fixed domains to the center of gravity of each cluster are calculated, then, the membership values of the respective particles to each cluster are calculated from these distances using a predetermined algorithm and the center of gravity of each cluster is calculated with a predetermined algorithm in consideration of the membership values. Thereafter, an interval between the new center of gravity and the preceding center of gravity is calculated and it is judged whether it is within a predetermined range or not. When it is not within the predetermined range, a further new center of gravity is calculated in the same manner from the distances from the new center of gravity to the respective particles outside the fixed domain and a similar judgement is effected on the interval between the newest center of gravity and its preceding center of gravity. When the above-mentioned interval comes within the predetermined range during repetition of this procedure, the number of particles belonging to each cluster is calculated with a predetermined algorithm from the membership values of the respective particles to the cluster which are variable at that time.

These and other features and operation of this invention will be described in more detail below about an embodiment thereof with reference to the accompanying drawings.

DESCRIPTION OF PREFERRED EMBODIMENTS

Figure 1:
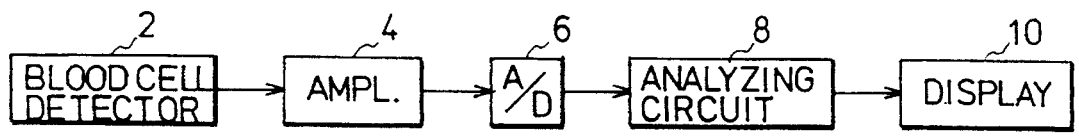
FIG. 1 is a block diagram showing a scheme of a device for embodying the method of this invention.

FIG. 1 shows a configuration of blood cell counting device in which a method of this invention is used for description of an embodiment of this invention. The device includes a blood cell detector 2 which is supplied with a specimen obtained by subjecting blood to preliminary treatments such as dilution and addition of hemolyzing agent for measuring properties of each blood cell and producing a corresponding detection signal, a amplifier 4 for suitably amplifying the detection signal, an analog-to-digital (A/D) convertor 6 for converting the amplified signal into a digital signal, an analyzing circuit 8 for analyzing the digital detection signal in accordance with the method of this invention and counting the number of blood cells of each kind and a display device 10 for displaying the result of analysis.

Figure 2A:
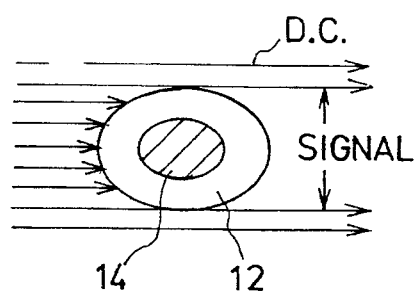
FIGS. 2a and 2b are diagrams showing two modes of detection in the blood cell detector of FIG. 1.
Figure 2B:
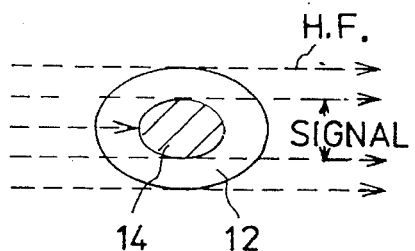

The blood cell detector 2 is a device, as disclosed, for example, in the U.S. Pat. No. 3,515,884, which is arranged to pass the specimen through a narrow path enabled to pass the blood cells one by one and apply d.c. and high frequency currents to the path, thereby deriving two kinds of signals based upon d.c. and high frequency impedance changes due to the respective blood cells. More particularly, in the case of d.c. current, a signal proportional to the size of a cytoplasm 12 of each blood cell as shown in FIG. 2a and, in the case of high frequency current, the detection signal is not so influenced by the cytoplasm 12 having low density and low impedance and has a value corresponding to the size and density of a nucleus or microsome 14 laving high density and high impedance as shown in FIG. 2b.

These two kinds of detection signals are amplified by the amplifier 4 and, then, converted by the A/D convertor 6 into digital signals for quantization. With this quantization, the signal of each blood cell derived by d.c. current is classified into any one of 256 channels (hereinunder referred to as "i" channel) numbered from 0 to 255 in accordance with its level and, similarly, the signal derived by high frequency current is classified into any one of 256 channels (hereinunder referred to as "j" channel) numbered from 0 to 255. Both kinds of digital signals are supplied to the analyzing circuit 8 which is composed of a personal computer or a microcomputer and accompanied by the display device 10 and a keyboard (not shown).

Figure 3:
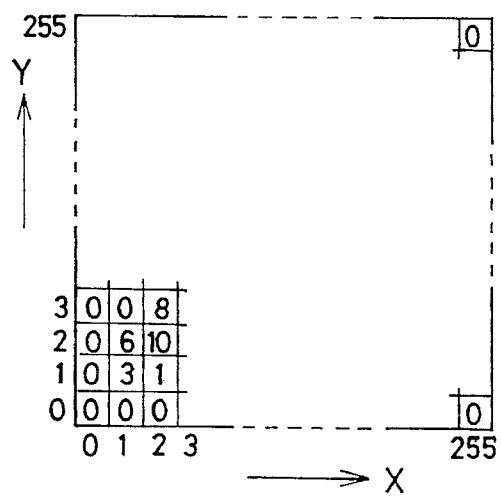
FIG. 3 is a diagram illustrative of a configuration of the scattergram used in the device of this invention.

The analyzing circuit 8 produces a scattergram, as shown in FIG. 3, having i and j channels on its X and Y axes, respectively. As shown, the scattergram includes $256^2$ basic elements (hereinunder referred to as "sites") having 256 X and Y co-ordinates, respectively, and each site stores the number of blood cells having the same co-ordinates as those of the site. For example, the value "6" stored in the site of X=1 and Y=2 in FIG. 3 means that there are six blood cells whose signal level attributable to the cytoplasm 12 is in the channel No. 1 and whose signal level attributable to the nucleus or microsome 14 is in the channel No. 2.

Figure 4:
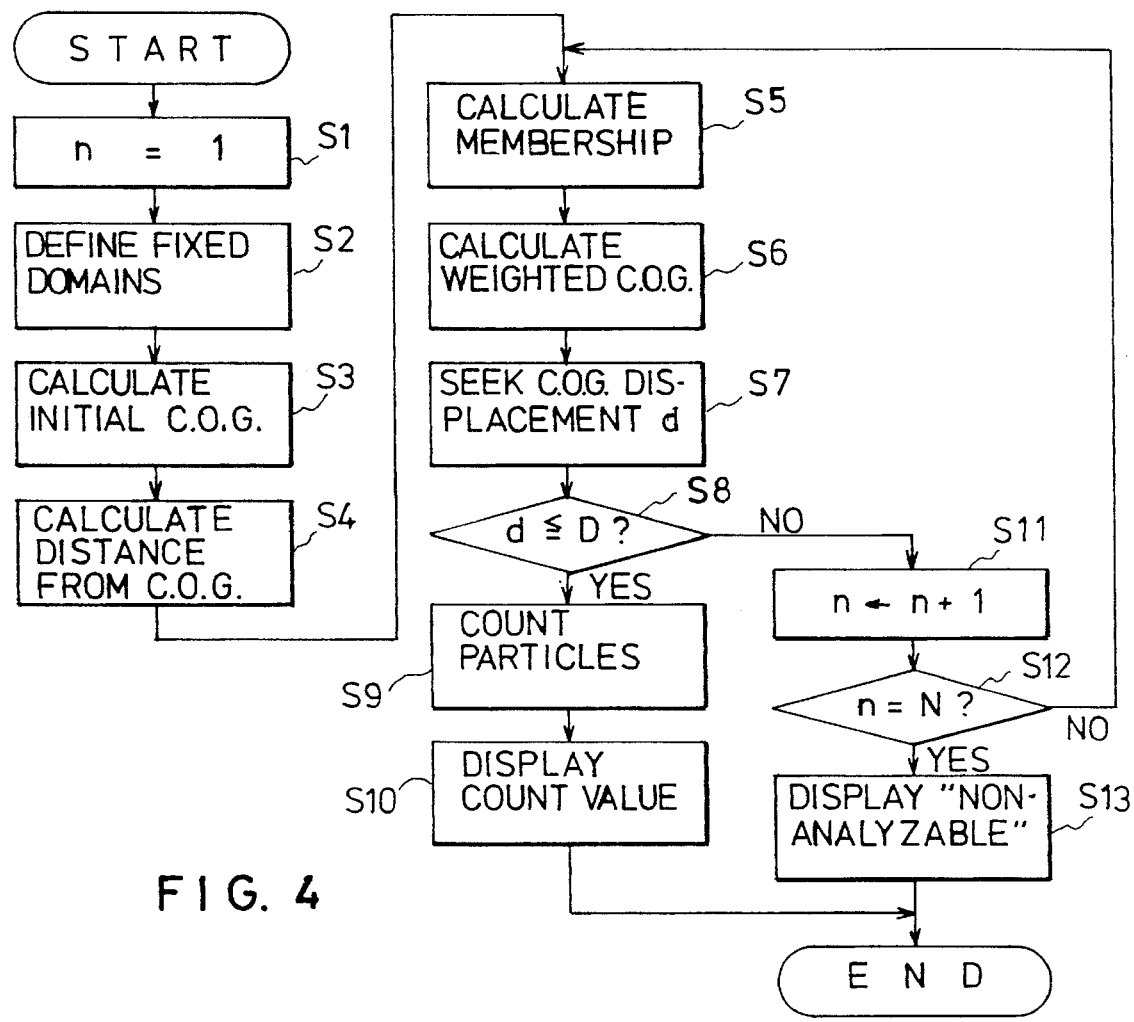
FIG. 4 is a flow chart for explaining processes executed in the analyzing circuit of FIG. 1.
Figure 5:
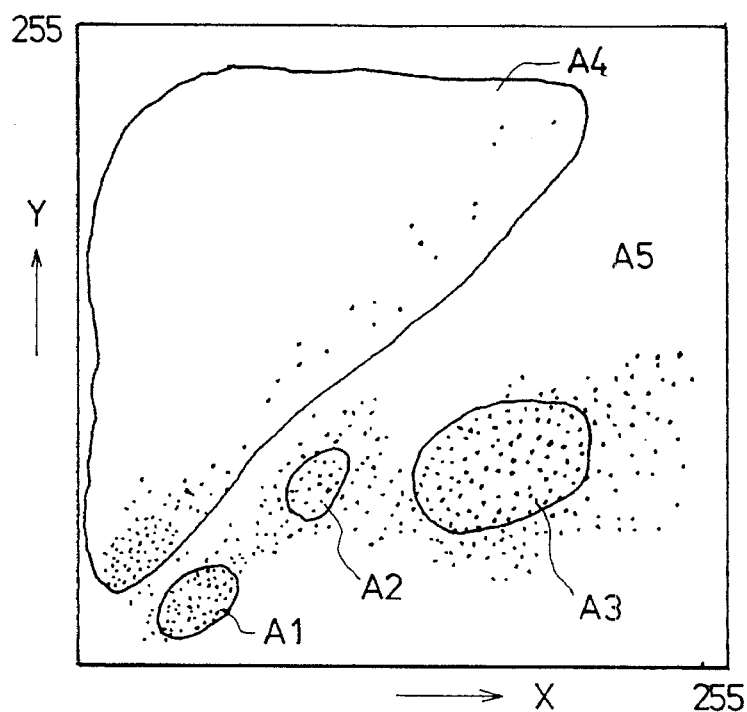
FIG. 5 is a diagram illustrative of definition of fixed domains for the respective clusters in an example of particle scattergram used in the embodiment of this invention.

Then, the analyzing circuit 8 executes an arithmetic processing as shown in the flow chart of FIG. 4. A memory value "n" representing the number of repetitions is set to one (step S1) and fixed domains A1, A2, A3 and A4 for the clusters of lymphocytes, monocytes, granulocytes and ghost cells such as red blood cells and platelets, respectively, which exist in the blood, are defined in the scattergram (step S2) These fixed domains are surrounded by such boundaries as shown in FIG. 5, for example, which are previously established experientially so that all particles within each boundary belong to the corresponding domain. In other words, all blood cells within each fixed domain A1, A2, A3 or A4 are lymphocytes, monocytes, granulocytes or ghost cells, respectively, while the cluster to which each blood cell in the external region A5 belong is indefinite. Therefore, it is herein assumed that the values of membership of the blood cells within the fixed domain A1 to the cluster of lymphocytes, the values of membership of the blood cells within the fixed domain A2 to the cluster of monocytes, the values of membership of the blood cells within the fixed domain A3 to the cluster of granulocytes and the values of membership of the blood cells within the fixed domain A4 to the cluster of ghost cells are all "one" and the blood cells in the region A5 belong to the four clusters at the same time at decimal values of membership, respectively. Then, the values of membership of each particle in the region A5 to the respective clusters are calculated in accordance with the following procedure.

Figure 6:
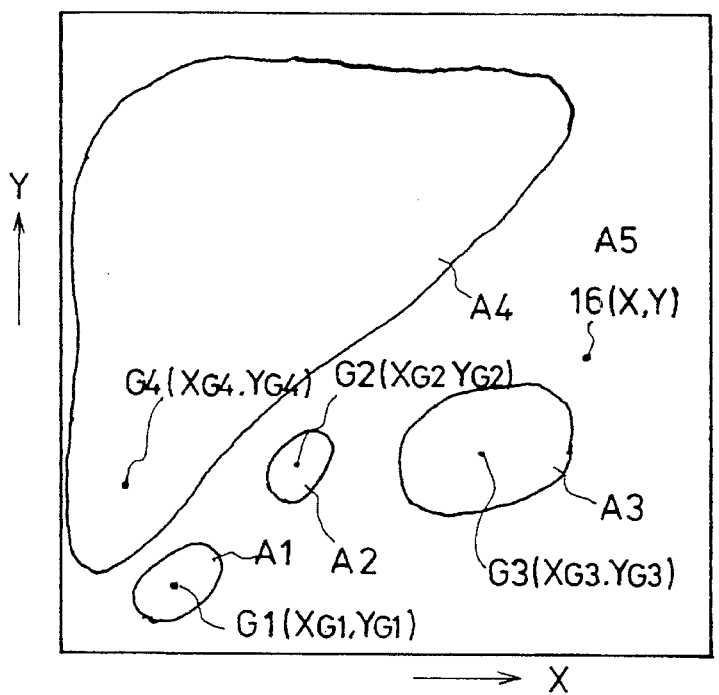
FIG. 6 is a diagram illustrative of the centers of gravity of the respective clusters in the particle scattergram of FIG. 5.

First, co-ordinates $X_G$ and $Y_G$ of an initial center of gravity (COG) of each cluster, which can be deemed to have all blood cells within the cluster concentrated thereto, are calculated (step S3). These co-ordinates can be calculated with the following equations.

$$X_G = \sum_i \sum_j N_{ij} \cdot i / \sum_i \sum_j N_{ij} \tag{1}$$

$$Y_G = \sum_i \sum_j N_{ij} \cdot j / \sum_i \sum_j N_{ij} \tag{2}$$

where $N_{ij}$ is the number of blood cells includes in each site within the fixed domain of each cluster. FIG. 6 show the initial centers of gravity $G1(X_{G1}, Y_{G1})$, $G2(X_{G2}, Y_{G2})$ $G3(X_{G3}, Y_{G3})$ and $G4(X_{G4}, Y_{G4})$ of the clusters of lymphocytes, monocytes, granulocytes and ghost cells, respectively, which have been obtained in this manner.

Figure 7:
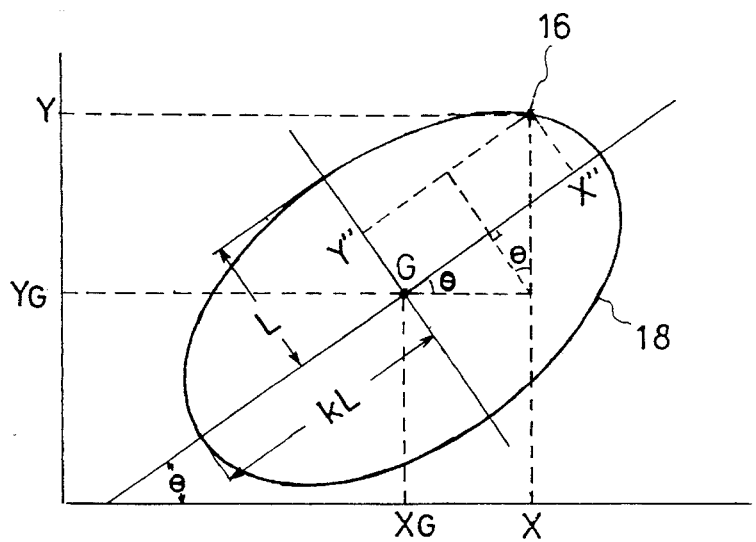
FIG. 7 is a diagram illustrative of a method of calculation of the distance from each particle to the center of gravity of each cluster in the particle scattergram.

Next, the distance from each particle in the region A5 to each initial center of gravity obtained as above is sought (step S4). This distance is not an Euclidean distance but one defined as as follows. Particularly, as shown in FIG. 7, the distance in question is defined as a half length L of the minor axis of an ellipse 18 having its center located at the initial center of gravity G of each cluster and its major axis tilted by an angle θ and passing the blood cell 16 in question. The tilt angle θ is peculiar to each cluster and determined previously in experimental fashion. The reason why (he distance is defined as above is that the shape of distribution of each cluster of blood cells is elliptic and, therefore, all blood cells lying on the same ellipse should have the same distance from the center of gravity. The calculation of the distance L is effected as follows. Defining co-ordinate axes X" and Y" along the major and minor axes of the ellipse 18, respectively, and assuming kL (k is a proportional constant) as the major axis of the ellipse 18, then, the equation of the ellipse is given as follows in connection with these co-ordinate axes.

$$\left(\frac{X''}{kL}\right)^2 + \left(\frac{Y''}{L}\right)^2 = 1 \tag{3}$$

This equation can be solved as follows as looking for the half minor axis or the distance L.

$$L = \sqrt{Y''^2 / \left(1 - \frac{X''^2}{k^2}\right)} \tag{4}$$

As is understood from FIG. 7, the relation between the co-ordinates X" and Y" and the original co-ordinates X and Y is given by the following equations.

$$X'' = \cos\theta(X - X_G) + \sin\theta(Y - Y_G) \tag{5}$$

$$Y'' = \cos\theta(Y - Y_G) - \sin\theta(X - X_G) \tag{6}$$

where X and Y are co-ordinates of the blood cell 16 in question, whose values are known as i and j. Putting these equations 5 and 6 into equation 4 and applying thereto the tilt angle e for each cluster, the distances $L_1$, $L_2$, $L_3$ and $L_4$ from tile blood cell 16 to the centers of gravity of the respective clusters are calculated.

Next, the value of membership $U_{16}$ of the blood cell to each cluster is calculated with the following equation.

$$U_{16} = \frac{\frac{1}{L}}{\frac{1}{L_1} + \frac{1}{L_2} + \frac{1}{L_3} + \frac{1}{L_4}} \quad (7)$$

where L is made $L_1$, $L_2$, $L_3$ or $L_4$ corresponding to each cluster. Each value of membership is, of course, less than one. In the same fashion, the values of membership of all blood cells within the region A5 to the respective clusters are calculated (step 5).

If $X-X_G=X'$ and $Y-Y_G=Y'$ in the above equations 5 and 6, X' and Y' represent a relative position of each blood cell with respect to each center of gravity. The operation time can be reduced by previously seeking this relative position of each blood cell for each cluster and storing them as a look up table.

As described above, each blood cell in the region A5 shares corresponding to its calculated values of membership. Therefore, the center of gravity of the respective clusters are corrected in consideration of weights of these blood cells or, in other words, weighted centers of gravity are calculated (step S6). This calculation can be effected with the following equations.

$$X_G' = \sum_i \sum_j U_{ij} N_{ij} \cdot i / \sum_i \sum_j U_{ij} N_{ij} \quad (8)$$

$$Y_G' = \sum_i \sum_j U_{ij} N_{ij} \cdot j / \sum_i \sum_j U_{ij} N_{ij} \quad (9)$$

By comparing each center of gravity thus obtained with the corresponding initial center of gravity, a displacement d therebetween is obtained (step S7). This value d is compared with the corresponding initial center of gravity to judge whether d is greater than D or not (step S8). The value D can be selected arbitrarily and may be zero. If d is not greater than D, it is concluded that attribution of all blood cells to the respective clusters has been decided. Accordingly, the number of blood cells in each cluster is herein decided by either one of two methods as follows (step S9). Selection of the method relies upon the state of the available scattergram.

In the first method, each blood cell in the region A5 is assumed to belong to a cluster exhibiting the greatest value of membership which is finally obtained for that blood cell. For example, when ten blood cells are included in a certain site and the values of membership of these blood cells to the clusters of lymphocites, monocytes, granulocytes and ghost cells, namely, $U_1$, $U_2$, $U_3$ and $U_4$ are 0.95, 0.03, 0.02 and 0.00, respectively, all of the ten blood cells are assumed to belong only to the cluster of lymphocytes of the greatest value of membership $U_1$. This method is suitable when the values of membership of the blood cells are especially large in a specific cluster and, in other words, the respective clusters are clearly separated.

In the another method, the blood cells in each site are allotted to the respective clusters in accordance with their values of membership. For example, when ten blood cells are included in a certain site and the values of membership $U_1$, $U_2$, $U_3$ and $U_4$ of these blood cells to the respective clusters are 0.2, 0.5, 0.3 and 0.0, respectively, the values of membership, excepting the cluster of ghost cells, are mutually close and suggest that the three clusters and partially overlapping. In such case, two, five, three and zero blood cell or cells are allotted to the clusters of lymphocytes, monocytes, granulocytes and ghost cells, respectively, by proportional distribution in accordance with their values of membership, since there should be a large counting error if the ten blood cells are allotted only to the cluster of monocytes having the greatest value of membership according to the first method. This method is effective when the respective cluster patterns are partially overlapping as above.

After the clusters having the respective blood cells allotted thereto are determined as above, the number of blood cells in each cluster is counted and displayed by the display device 10 (step S10).

If d is greater than D in step S 8, the stored value n is raised by one (step S11) and the resultant value is compared with a predetermined value N (step S12). If n has not yet reached N, returning to step S5, a similar operation is repeated. If n has reached N in step S12, the display device 10 displays "ANALYSIS IMPOSSIBLE" (step 13).

As described above, the position of the center of gravity of each cluster and the major and minor axes of the ellipse which suggest its state of spread are calculated during the operation of the analyzing circuit 8. Therefore, by comparing these values with predetermined normal values, their deviations, that is, a state of health can be diagnosed.

When the above embodiment was executed in practice by using a commercially available 32 bit personal computer as the analyzing circuit 8 and setting the above-mentioned predetermined number of repetition to three times, a result which would be satisfactory in practical use was obtained within a short time such as ten seconds almost regardless of the state of scattergram.

The above embodiment has been presented only for the purpose of illustration of the invention and it does not mean any limitation of the invention. It should be easily understood by those skilled in the art that various modifications, variations and changes can be made thereon within the scope of this invention as defined in the appended claims. For example, it is a matter of course that this invention can be applied not only to blood cells but also to many kinds of other particles, though it is applied to clustering and counting blood cells in the above embodiment. While, in the embodiment, the distance from the center of gravity of each cluster to each particle is defined as non-Euclidean, it may be Euclidean in some cases of other kind of particles. Moreover, while the blood cell detector 1 in the above embodiment utilizes difference in d.c. and high frequency impedance of various blood-cells, it may be one utilizing difference in light scattering and fluorescent characteristics as the flow cytometer which is disclosed, for example, in the U.S. Pat. No. 4,661,913. However, the structure of the blood cell detector is not the subject of this invention and, in short, it is enough for use if it can derive two or more kinds of signals from each particle. Although a two-dimensional scattergram is used in the above embodiment, a three-dimensional scattergram can be used if three kinds of signals are available. Furthermore, in general, any dimensional scattergram can be utilized theoretically, apart from the problem of complicated arithmetic operation, and these are also within the scope of this invention.

I claim:

1. A particle counting apparatus, comprising:

a particle detector comprising a path for receiving a specimen, said specimen containing a plurality of particles and plural kinds of particles, said detector generating signals representing at least two characteristics of each of said plurality of particles when said plurality of particles pass through said path;

an analyzer for analyzing said signals generated by said particle detector, said analyzer comprising:

means for generating a scattergram having at least two dimensions, said scattergram being based on said signals generated by said particle detector;

means for defining a plurality of fixed domains in said scattergram, said fixed domains containing said particles, said particles belonging to respective clusters, said clusters corresponding to respective ones of said plural kinds of particles, and assigning a membership value of one to the particles within said fixed domains;

means for determining a center of gravity of each of said clusters based on a spatial distribution of the particles in each fixed domain;

means for determining distances of particles distributed outside said fixed domains to the center of gravity of each cluster and calculating a membership value for each of said particles distributed outside the fixed domains to each cluster based on said determined distance;

means for correcting the center of gravity of each cluster based on the membership values of the particles distributed outside the fixed domains to each cluster and the membership values of the particles within each fixed domain;

means for causing said means for calculating membership values to repeat operation based on said corrected center of gravity and for causing said means for correcting the center of gravity to repeat operation based on membership values obtained by repeating calculation of membership values until an mount of correction of the center of gravity reaches a predetermined value; and means for estimating a number of particles that belong to each cluster based on the membership value of each particle to each cluster; and a display for displaying results obtained by the analyzer.

2. The particle counting apparatus of claim 1, wherein said analyzer is a programmable, general purpose computer.

3. The particle counting apparatus of claim 3, wherein said means for determining distances of particles distributed outside the fixed domains calculates said distances as a half-length of a minor axis of an ellipse having its center at the center of gravity of each cluster and having a predetermined ratio of the major and minor axes and the tilt angle of the major axis of the ellipse for each cluster for which the particle subject to distance calculation is positioned.

4. The particle counting apparatus of claim 1, wherein said particles are different types of blood corpuscles.

* * * * *